United States Patent [19]
Tanaka et al.

[11] Patent Number: 4,894,343
[45] Date of Patent: Jan. 16, 1990

[54] CHAMBER PLATE FOR USE IN CELL FUSION AND A PROCESS FOR PRODUCTION THEREOF

[75] Inventors: Shinji Tanaka, Akishima; Kazuo Sato, Tokyo; Tsuneo Terasawa, Hachioji; Yoshio Kawamura, Kokubunji; Hisashi Tsuruoka, Hachioji, all of Japan

[73] Assignee: Hitachi, Ltd., Tokyo, Japan

[21] Appl. No.: 122,269

[22] Filed: Nov. 18, 1987

[30] Foreign Application Priority Data
Nov. 19, 1986 [JP] Japan .................. 61-274031

[51] Int. Cl.$^4$ ............................................. C12M 1/20
[52] U.S. Cl. ..................................... 435/301; 435/300; 435/311; 422/101; 422/102; 210/498; 935/93
[58] Field of Search ............. 210/498, 500.25, 500.26, 210/503, 505; 435/287, 300, 301, 311; 935/93; 422/101, 102

[56] References Cited
U.S. PATENT DOCUMENTS

| | | | |
|---|---|---|---|
| 790,043 | 5/1905 | Fiedler et al. | 210/498 X |
| 3,359,192 | 12/1967 | Heinrich et al. | 210/498 X |
| 3,482,703 | 12/1969 | Roberts et al. | 210/498 X |
| 3,957,652 | 5/1976 | McGonigal | 210/498 |
| 4,441,972 | 4/1984 | Pohl | 204/183.1 |
| 4,473,466 | 9/1984 | Schmidt et al. | 209/397 |
| 4,729,949 | 3/1988 | Weinreb et al. | 435/30 |
| 4,746,962 | 5/1988 | Yamazaki | 357/30 |
| 4,785,191 | 11/1988 | Ondris | 250/578 |

Primary Examiner—Martin P. Schwadron
Assistant Examiner—Allen J. Flanigan
Attorney, Agent, or Firm—Antonelli, Terry & Wands

[57] ABSTRACT

There are disclosed a chamber plate for use in cell fusion comprising a plate of single crystal silicon on which a plurality of chambers for holding at least a pair of unit cells are formed in array, said chamber having at the bottom a plate having slits which do not pass cells to be held; and a process for producing a chamber plate for use in cell fusion which comprises forming chambers for holding cells in a plate of single crystal silicon by anisotropic etching or isotropic etching by chemical etching.

5 Claims, 11 Drawing Sheets

4,894,343

CHAMBER PLATE FOR USE IN CELL FUSION AND A PROCESS FOR PRODUCTION THEREOF

BACKGROUND OF THE INVENTION

This invention relates to a chamber plate for use in the fusion of biological cells and a process for production thereof.

A prior art in which cells are aligned one by one is disclosed, for example, in Japanese Patent Kokai (Laid-Open) No. 251877/85.

The above-mentioned prior art discloses that when cells are supplied one by one and aligned and, for example, microinjection of cells, or observation under an electron microscope is carried out, the cells are introduced into an assortment case in order to align or immobilize them one by one. However, the assortment case is not investigated in detail, and how to make an assortment case having a size suitable for holding individual cells is not disclosed at all.

On the other hand, there is also a method for immobilizing cells using poly-L-resin, but the toxicity of poly-L-resin is feared. One cause of a lowering of the activity of the cells is that there is no suitable means for holding cells stably while maintaining the activity of the cells.

SUMMARY OF THE INVENTION

The object of this invention is to provide a chamber plate for aligning a large amount of cells on a plane in a short time, forming a large number of cell pairs, holding them while stabilizing their positions with certainty, and fusing the cells; and a process for producing the same.

The above object can be achieved by forming a high-precision alignment pattern of holes on a plate of single crystal silicon by lithography, then forming a large number of chambers by anisotropic etching or isotropic etching by chemical etching, and thereby obtaining a chamber plate.

Plates of single crystal silicon make it possible to enhance the precision of positional relation of the regular alignment in an apparatus for holding fine particles by utilizing a lithography technique, and facilitate formation of chambers to isolate cells of three-dimensional complicated form by anisotropic etching. The silicon plate on which the chambers have been formed securely isolates at least a pair of cells to be fused. Silicon plates are not disadvantageous from the viewpoint of toxicity to cells.

DETAILED DESCRIPTION OF THE PREFERRED EMBODIMENTS

Figure 1:
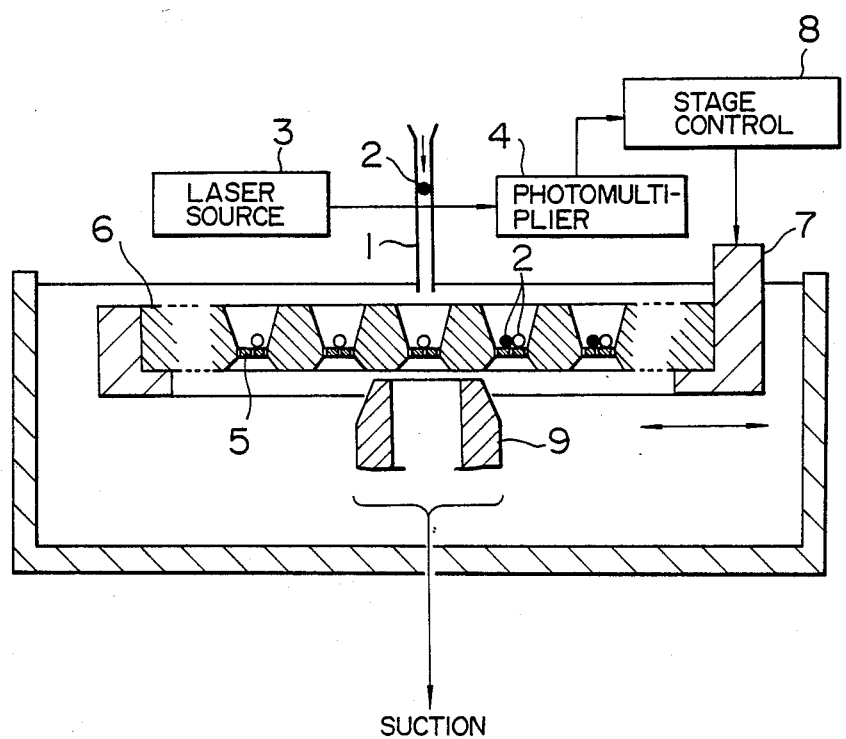
FIG. 1 is a schematic view of an instrument for carrying out one-to-one cell fusion.
Figure 2A:
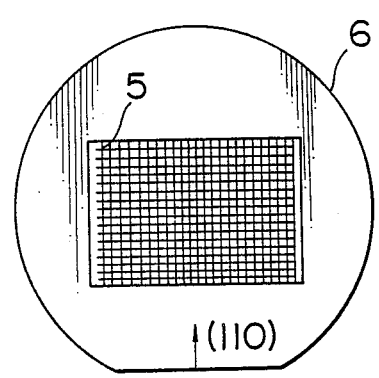
FIG. 2A is a front view of a chamber plate for use in cell fusion obtained by forming a large number of chambers on a silicon plate.
Figure 2B:
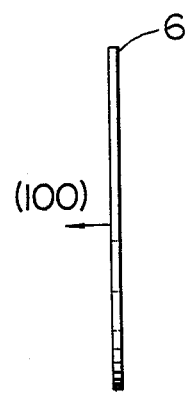
FIG. 2B is a side view corresponding to FIG. 2A.

This invention is illustrated below by way of embodiments. FIG. 1 shows the structure of an instrument for forming pairs of two different kinds of cells and carrying out cell fusion. In FIG. 1, cells 2 which pass through a sample nozzle 1 are detected by an optical system composed of laser source 3 and a photomultiplier 4, and the cells are individually introduced into each small compartment (chamber) 5. A stage 7 holding a chamber plate 6 having the chambers 5 is controlled by a stage controlling device 8, and a predetermined chamber 5 is positioned under the sample nozzle 1. By repeating this procedure, pairs of two kinds of cells can be formed and it becomes possible to carry out one-to-one cell fusion in each chamber 5. The chamber 5 is required to have a structure having slits which capture cells and pass a water flow, and a suction nozzle 9 for introducing cells satisfactorily into the chambers 5 is provided. FIG. 2A and FIG. 2B show a substrate in which said chambers 5 are arranged in array, namely, the chamber plate 6 for use in cell fusion of this invention. In FIG. 2A and FIG. 2B, this chamber plate 6 comprises a plate of single crystal silicon, and concave chambers 5 for housing and holding cells are formed in the plate. This chamber plate can be operated while holding a large number of cells individually in isolated state in the chambers 5 aligned on the plate. It is also possible to introduce a pair of cells into the chamber 5 and fuse them.

Figure 3A:
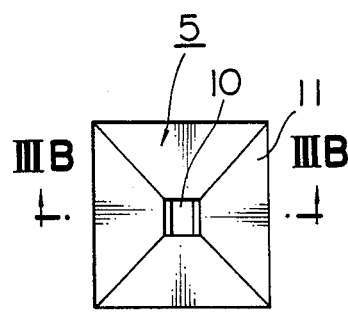
FIG. 3A is a front view showing a chamber of one embodiment of this invention.
Figure 3B:
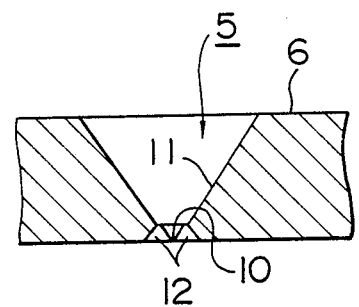
FIG. 3B is a cross-sectional view along the IIIB—IIIB line in FIG. 3A.
Figure 4A:
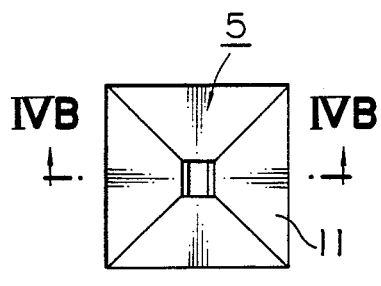
FIG. 4A is a front view showing a chamber of another embodiment of this invention.
Figure 4B:
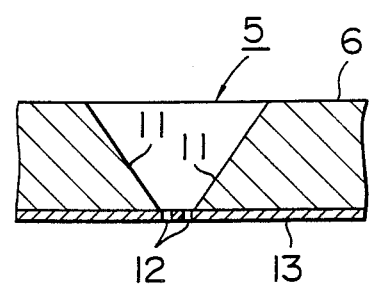
FIG. 4B is a cross-sectional view along the IVB-IVB line in FIG. 4A.

Next, the shape of the above-mentioned chamber is described below in detail. FIGS. 3A and 3B show the shape of a chamber 5 obtained when the plane orientation of the plate of single crystal silicon is (100), and this chamber 5 has walls 11 isolating cells individually or in pairs and a bottom plate or wall 10 having a sufficient strength for holding the cells. Slits 12 are formed in a part of the bottom plate 10 so as to impart a structure which holds only cells and passes a fluid, whereby cell manipulation in a liquid becomes possible. As shown in FIGS. 4A and 4B, an oxide film ($SiO_2$) 13 can be used in place of the bottom plate 10. The oxide film 13 is transparent and when a chamber 5 having the oxide film 13 at the bottom is used, the condition of cell can be observed under a microscope or the like, so that not only cell fusion but also cell manipulation and microinjection become easy.

Figure 5A:
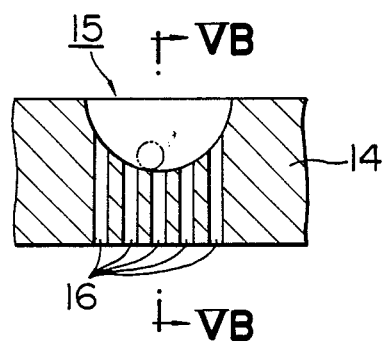
FIG. 5A is a cross-sectional view of a chamber showing further another embodiment of this invention.
Figure 5B:
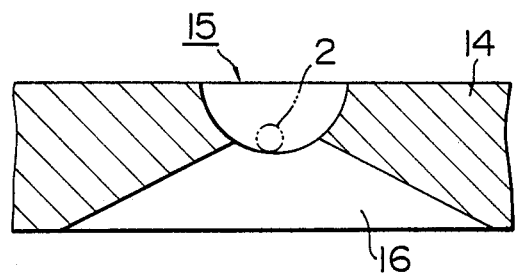
FIG. 5B is a cross-sectional view along the VB—VB line in FIG. 5A.

Next, the shape of chambers formed in a plate of single crystal silicon having a plane orientation of (110) is shown in detail in FIGS. 5A and 5B. The chamber has a structure in which as shown in FIG. 5A, a semispherical hole 15 for introducing cells is formed on one side of the plate 14, and slit-like deep holes 16 start from the other side and lead to the semispherical hole. In the side section, as shown in FIG. 5B, the deep hole 16 is formed so as to extend from the semispherical hole.

Figure 6A:
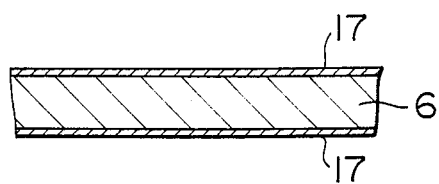
FIGS. 6A to 6L are cross-sectional views showing a production process of the chamber shown in FIGS. 3A and 3B.
Figure 6B:
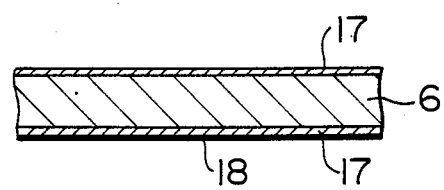
Figure 6C:
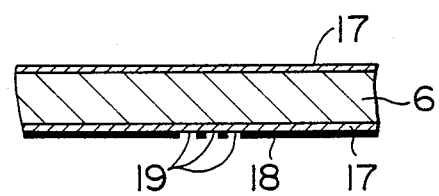
Figure 6D:
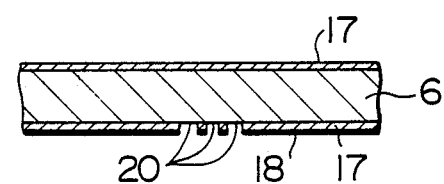
Figure 6E:
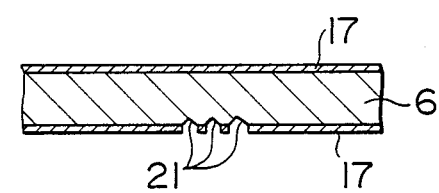
Figure 6F:
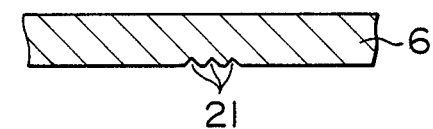
Figure 6G:
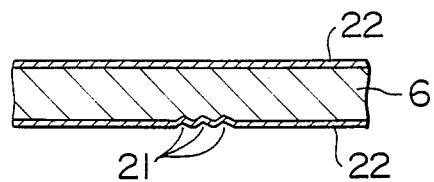
Figure 6H:
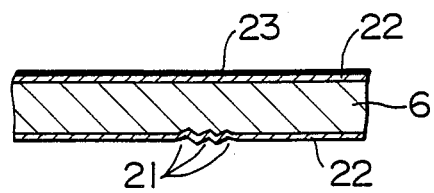
Figure 6I:
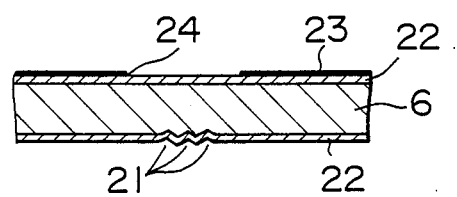
Figure 6J:
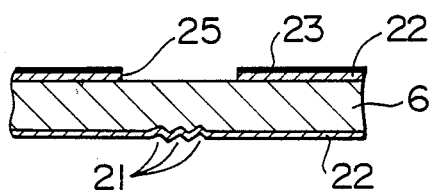
Figure 6K:
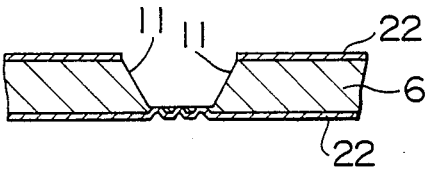
Figure 6L:
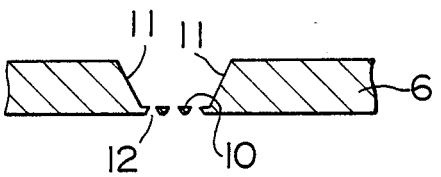

Next, a production process regarding the shape of chambers mentioned above is described below in detail. FIGS. 6A to 6L show a process for forming a chamber as shown in FIGS. 3A and 3B. First, an oxide film 17 is formed on each side of a substrate 6 (FIG. 6A). Then, a photoresist 18 is coated on one side (FIG. 6B). Subsequently, a pattern 19 is formed in a photoresist 18 by exposure to light using a projection aligner and development (FIG. 6C), after which the oxide film 17 is etched with hydrofluoric acid or the like by using as a mask the resist 18 having the pattern 19, whereby a perforated pattern 20 is formed in the oxide film 17 (FIG. 6D). After the resist 18 is removed, the substrate 6 is subjected to anisotropic etching by use of an aqueous KOH solution to form 111 plane, whereby the grooves shown in FIG. 6E are formed. Then, the oxide films 17 are removed (FIG. 6F), and an oxide film 22 is again formed on each whole surface (FIG. 6G). A resist 23 is coated on the side reverse to the side on which the grooves have been formed (FIG. 6H), after which by the same procedure as described above, a perforated pattern 25 is formed in the resist 23 (FIG. 6I) and a rectangular perforated pattern 24 is formed in the oxide film 22 (FIG. 6J). After the resist 23 is removed, anisotropic etching is conducted for a suitable period of time, whereby a partially perforated bottom plate is formed (FIG. 6K). Finally, the oxide films 22 are removed to form slits 12 which pierce the subtrate 6 substantially (FIG. 6L). Then, the chamber plate thus produced is used. It is also possible to use the chamber plate after subjecting the same to surface treatment such as formation of an oxide film on the whole surface. Although silicon oxide is used as a mask in the embodiment described above, silicon nitride may be used in place of silicon oxide.

Figure 7A:
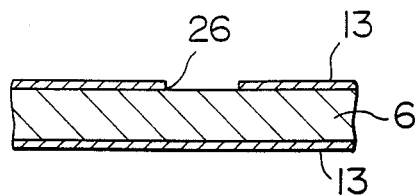
FIGS. 7A to 7E are cross-sectional views showing a production process of the chamber shown in FIGS. 4A and 4B.
Figure 7B:
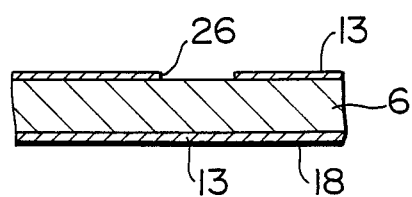
Figure 7C:
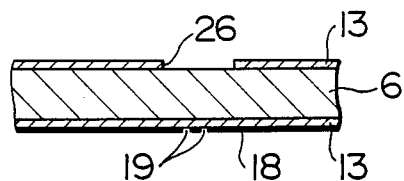
Figure 7D:
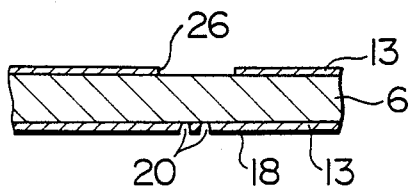
Figure 7E:
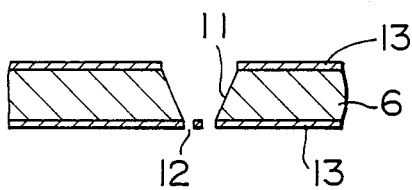

Next, a process for forming the chamber having an oxide film as its bottom portion shown in FIG. 4A and FIG. 4B is described below with reference to FIGS. 7A to 7E. As in the process shown in FIG. 6A, an oxide film 13 is formed on each side of a substrate, and a rectangular pattern 26 is formed on one side (FIG. 7A). Then, a resist 18 is formed (FIG. 7B), after which a resist pattern 19 is formed therein so as to be in a desired positional relation with the rectangular perforated pattern 26 on the one side (FIG. 7C), and a partially perforated pattern 20 is formed on the other side (FIG. 7F). Finally, the resist 18 is removed and etching with an aqueous KOH solution is conducted using the oxide film 13 as a mask, to obtain a chamber having a desired shape (FIG. 7E).

Figure 8A:
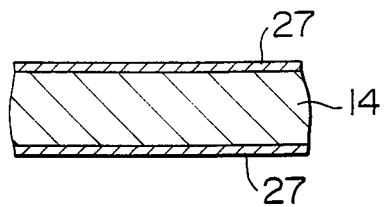
FIGS. 8A to 8K are cross-sectional views showing a production process of the chamber shown in FIGS. 5A and 5B.
Figure 8B:
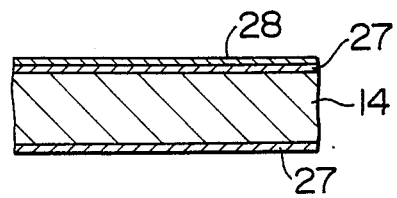
Figure 8C:
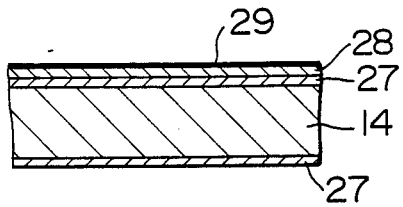
Figure 8D:
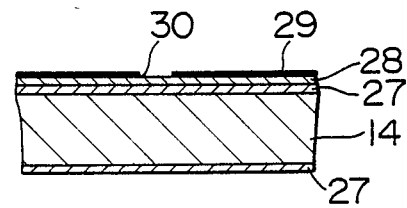
Figure 8E:
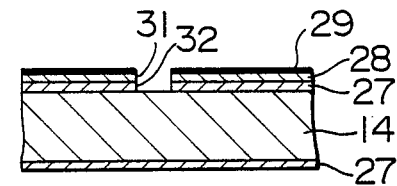
Figure 8F:
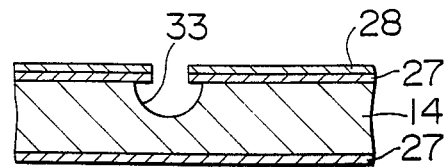
Figure 8G:
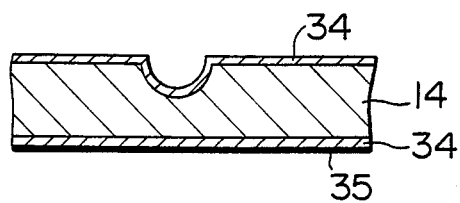
Figure 8H:
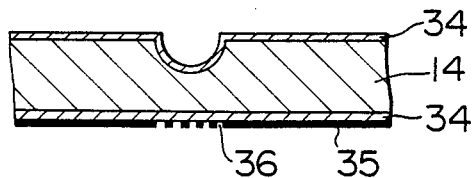
Figure 8I:
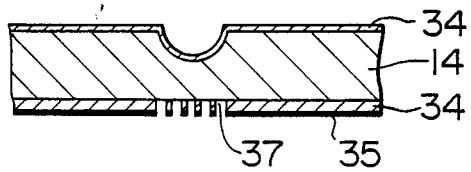
Figure 8J:
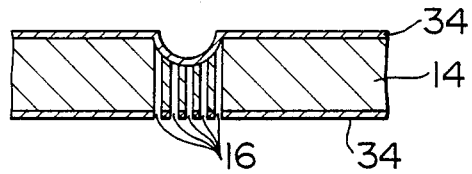
Figure 8K:
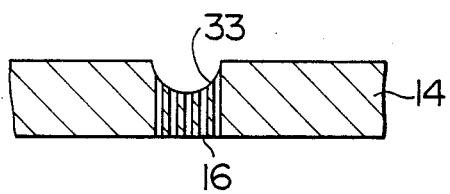

Next, a process for forming the chamber shown in FIGS. 5A and 5B is explained with reference to FIGS. 8A to 8K. As in the embodiments described above, an oxide film 27 is formed on each side of a wafer of single crystal silicon 14 (FIG. 8A). Then, deposits 28 of chromium and gold are formed on one side of the wafer (FIG. 8B). After a resist 29 is coated on the deposits 28 (FIG. 8C), exposure by means of a projection aligner and development are carried out to form a circular perforated pattern 30 (FIG. 8D). Subsequently, using the resist 29 as a mask, apart of the deposits of gold and chrominum are removed by use of an aqueous ammonium iodide solution and an aqueous ammonium ceric nitrate solution, respectively, to form a circular pattern 31 (FIG. 8E). Next, the oxide film is etched to obtain a circular pattern 32 (FIG. 8E). After the resist 29 is removed, the silicon is subjected to isotropic etching with a mixed solution of hydrofluoric acid and nitric acid by using the residual deposits of chromium and gold and the oxide film 27 as masks, whereby a semispherical cavity 33 is formed (FIG. 8F). Then, the deposits 28 of gold and chromium and the oxide film 27 are removed and an oxide film 34 is newly formed on each side of the wafer 14, after which a resist 35 is coated on one side (FIG. 8G). By the same procedure as in the embodiments described above, a perforated pattern 36 of the resist is formed on the surface reverse to the surface on which the semispherical cavity 33 has been formed, after which a perforated pattern 37 of the oxide film is formed (FIG. 8I). The resist 35 is removed and anisotropic etching is conducted with an aqueous KOH solution by using the oxide film as a mask (FIG. 8J). In this case, parallel grooves according to the pattern 16 can be formed by properly selecting the direction of pattern and the crystal orientation of the wafer of single crystal silicon. Finally, the oxide films 34 are removed to obtain a semispherical cavity 33 having drain slits 16 (FIG. 8K).

Figure 9:
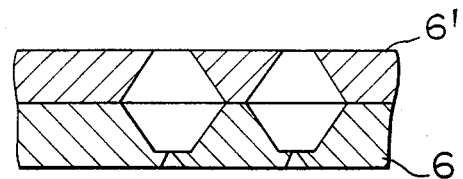
FIG. 9 and FIG. 10 are cross-sectional views showing a chamber having a laminated structure.
Figure 10:
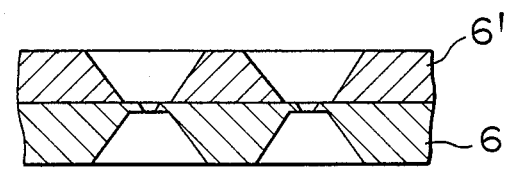

Although chambers are formed in a single plate of single crystal silica in the embodiments described above, a structure in which chamber plates 6 and 6' are combined as shown in FIG. 9 are also easily practicable according to this invention. From this invention, there can also easily thought of employment of a laminated structure composed, as shown in FIG. 10, of the chamber plate 6 shown in FIG. 3B and another chamber plate 6', said chamber plate 6 being combined up side down with the chamber plate 6'. Furthermore, it is also easy to carry out a change to a laminated structure composed of a plate of single crystal silicon having chambers formed therein and a plate of other material such as a glass plate. Moreover, although in the embodiments described above, a description is given only for two kinds of plates of single crystal silicon having plane orientations of (100) and (110), respectively, this invention is applicable also to substrates having other plane orientations.

Although in the embodiment described above, isotropic etching and anisotropic etching by wet methods are employed as methods for etching, chambers for housing and holding cells can be formed also by processing by dry etching.

Figure 11:
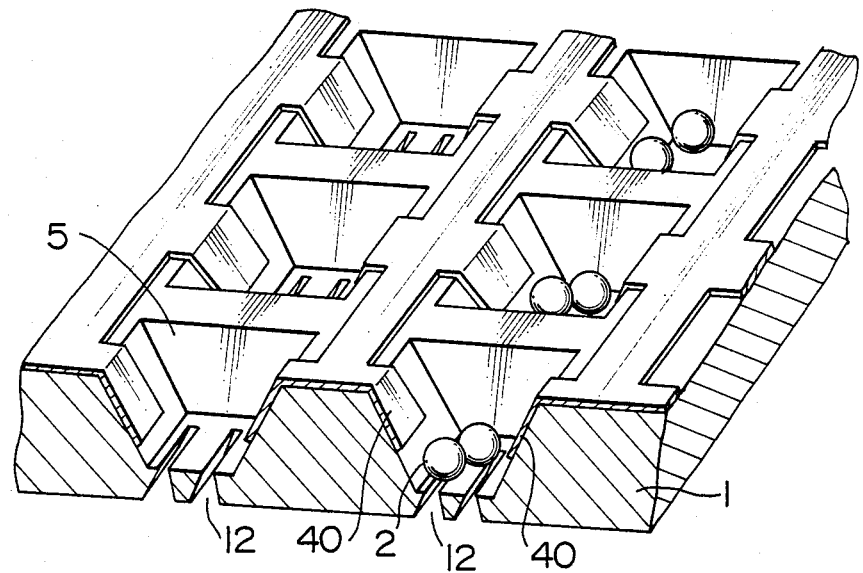
FIG. 11 is a partially sectioned bird's-eye view of a chamber plate in which electrodes are formed.
Figure 12:
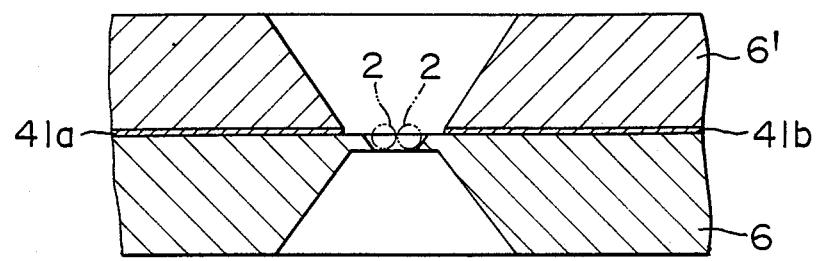
FIG. 12 is a cross-sectional view of a laminated chamber plate in which electrodes are formed at the joint interface.

Next, a method for fusing pairs of cells in the chambers shown in the embodiment described above is explained below. FIG. 11 shows chambers 5 in each of which electrodes 40a and 40b are formed. A pair of cells 2 introduced into the chamber 5 can be brought into contact with each other in pearl chain by applying a high-frequency voltage (about 0.5 MHz to about 3 MHz) between the electrode 40a and the electrode 40b. When the base area of the chamber is made sufficiently small, the cells 2 can be kept in contact with each other. The two cell can be fused by applying a pulsating direct current voltage between the electrodes 40a and 40b for a short period of time which keeping the cells 2 in contact with each other. Although in FIG. 11 is shown a structure in which a pair of electrodes are formed on the side walls, there can be thought of various other manners in which electrodes are formed. It is also possible to form, as shown in FIG. 10, a laminated structure in which electrodes 41a and 41b are formed on a plane as shown in FIG. 12.

Figure 13:
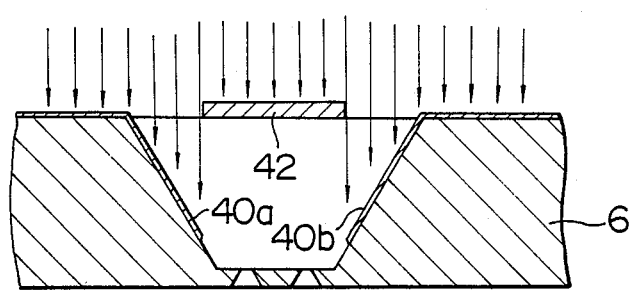
FIG. 13 is a cross-sectional view showing a chamber in which electrodes are formed by a vacuum evaporation method.

Next, a method for forming the electrodes 40a and 40b shown in the above embodiment is described below. As shown in FIG. 13, the electrodes 40a and 40b are formed by placing a screen 42 on the side on which the cavity 5 of the chamber plate 6 has been formed, and laminating a metal such as Al or Pt by vacuum evaporation from the direction of arrows in FIG. 13.

Figure 14:
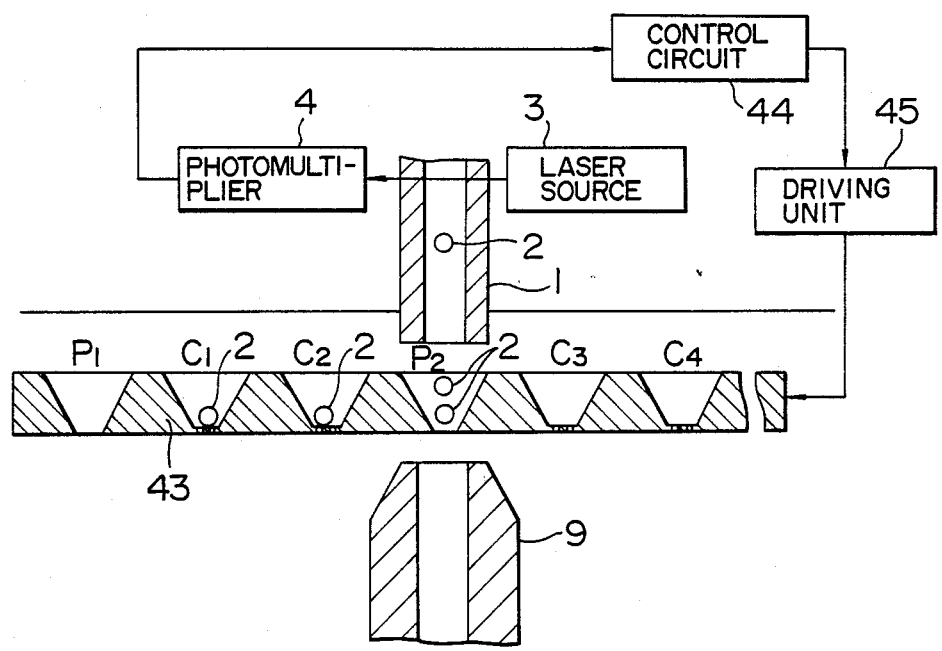
FIG. 14 is a schematic view showing an instrument constructed so as to supply only one cell to each chamber by means of a chamber plate having chambers and exclusion holes.

Next, a chamber plate 43 for introducing one cell into each chamber with certainty is described below. FIG. 14 shows the chamber plate 43 having chambers ($C_1$ to $C_4$) into which cells 2 are introduced and holes $P_1$ and $P_2$ for discharging cells. In this case, cells 2 which pass through a sample nozzle 1 scatter laser beam from a laser source 3. A photomultiplier 4 detect the magnitude of the scatter of laser beam caused in this case and discriminate among a single cell 2, a chain of a plurality of cells 2, and other foreign substances such as dust. In order to introduce one cell to each chamber, particles other than a single cell should be discharged through holes ($P_1$, $P_2$, -----). Therefore, when an unnecessary particle is recognized, this information is fed back to a driving unit 45 of X-Y table through processing in a control circuit 44, and the chamber plate 43 is moved so that the nozzle 1 is above the nearest among the holes ($P_1$, $P_2$, -----) for excluding the cells. As a result, among cells 2 to be supplied, only independent cells 2 which are not linked together in chain can be introduced to chambers so as to introduce only one cell to each chamber. By subjecting another type of cells to this procedure, a pair of different types of cells can be formed in each chamber.

Although in the embodiments described above, a description was made for an one-dimensional array of chamber, this invention can be conducted also for a two-dimensional array according to the same conception as described above.

As is clear from the explanation given above, in the case of the apparatus for holding fine particles of this invention, complicated and fine holes can be formed by a means such as anisotropic etching or isotropic etching by using a plate of single crystal silicon, so that objective cells can be isolated and held stably with certainty. Consequently, one-to-one cell fusion becomes possible. In addition, because of single crystal silicon, said plate is uniformly excellent in mechanical strength, and moreover a large number of chambers or cavities can be aligned therein in an accurate positional relation by lithography technique. In order to align particles more stably, it is also possible to form electrodes for sucking particles on the bottom plate of each already formed chamber. Consequently, said apparatus makes it possible to manipulate cells in a large amount rapidly and effectively when mounted in a biotechnological instrument such as instrument for cell fusion, and is effective in automatic manipulation of cells.

What is claimed is:

1. A chamber plate for use in the fusion of biological cells comprising a plate of single crystal silicon in which a plurality of chambers for holding at least a pair of unit cells is formed in an array, each of said chambers having side and bottom walls for isolating the cells and for defining a base area keeping the cells in contact with each other, the bottom wall having a slit which allows passage of fluid, but which does not allow passage of the cells.

2. The chamber plate for use in cell fusion according to claim 1, wherein each chamber is composed of side walls made of silicon of the plate of single crystal silicon and a bottom wall made of an optically transparent substance.

3. The chamber plate for use in cell fusion according to claim 1, wherein electrodes for causing fusion of cells held in each chamber of said plate of single crystal silicon are formed in a part of the chamber.

4. The chamber plate for use in cell fusion according to claim 1, wherein holes for excluding cells are provided along sides of the chambers for isolating said cells.

5. The chamber plate for use in cell fusion according to claim 1, wherein the chambers of said plate of single crystal silicon are formed by anisotropic etching.

* * * * *